US010881875B2

(12) United States Patent
Ranganathan et al.

(10) Patent No.: US 10,881,875 B2
(45) Date of Patent: Jan. 5, 2021

(54) PRE-OPTIMIZATION METHOD FOR QUICK PREDICTION OF ACHIEVABILITY OF CLINICAL GOALS IN INTENSITY MODULATED RADIATION THERAPY

(71) Applicant: KONINKLIJKE PHILIPS N.V., Eindhoven (NL)

(72) Inventors: Vaitheeswaran Ranganathan, Bangalore (IN); Prashant Kumar, Bangalore (IN); Karl Antonin Bzdusek, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 36 days.

(21) Appl. No.: 16/076,721

(22) PCT Filed: Mar. 1, 2017

(86) PCT No.: PCT/EP2017/054680
§ 371 (c)(1),
(2) Date: Aug. 9, 2018

(87) PCT Pub. No.: WO2017/153211
PCT Pub. Date: Sep. 14, 2017

(65) Prior Publication Data
US 2019/0038916 A1    Feb. 7, 2019

Related U.S. Application Data

(60) Provisional application No. 62/305,647, filed on Mar. 9, 2016.

(51) Int. Cl.
*A61N 5/10* (2006.01)
*A61B 6/00* (2006.01)

(52) U.S. Cl.
CPC .............. *A61N 5/1031* (2013.01); *A61B 6/50* (2013.01); *A61B 6/5294* (2013.01); *A61N 5/1045* (2013.01); *A61N 2005/1074* (2013.01)

(58) Field of Classification Search
CPC ................ A61N 5/1031; A61N 5/1045; A61N 2005/1074; A61B 6/50; A61B 6/5294
See application file for complete search history.

(56) References Cited

U.S. PATENT DOCUMENTS

2002/0051513 A1 *  5/2002  Pugachev .............. A61N 5/103
378/65
2004/0001569 A1 *  1/2004  Luo ...................... A61N 5/1031
378/65

(Continued)

FOREIGN PATENT DOCUMENTS

JP    2014023741 A  *  2/2014
WO   2015193776       12/2015

OTHER PUBLICATIONS

Amit, et al., "Automatic Learning-Based Selection of Beam Angles in Radiation Therapy of Lung Cancer", Med. Phys. 42 (4), Apr. 2015.

(Continued)

*Primary Examiner* — Taeho Jo (57) ABSTRACT

An achievability estimate is computed for an intensity modulated radiation therapy (IMRT) geometry (32) including a target volume, an organ at risk (OAR), and at least one radiation beam. Namely, a geometric complexity (GC) metric is computed for the IMRT geometry that compares a number NT of beamlets of the at least one radiation beam available in the IMRT geometry for irradiating the target volume and a number n of these beamlets that also pass through the OAR. A GC metric ratio is computed of the GC metric for the IMRT geometry and the GC metric for a reference IMRT geometry for which an IMRT plan is (Continued)

achievable. If the clinician is satisfied with this estimate then optimization (38) of an IMRT plan for the IMRT geometry (32) is performed. Alternatively, a reference IMRT geometry is selected by comparing the GC metric with GC metrics of past IMRT plans.

20 Claims, 6 Drawing Sheets

(56) References Cited

U.S. PATENT DOCUMENTS

| | | | |
|---|---|---|---|
| 2005/0123098 A1* | 6/2005 | Wang | A61N 5/1031 378/151 |
| 2007/0201614 A1 | 8/2007 | Goldman | |
| 2008/0123813 A1* | 5/2008 | Maurer | G21K 1/046 378/96 |
| 2011/0085643 A1 | 4/2011 | Zhu | |
| 2011/0122997 A1* | 5/2011 | Lu | A61N 5/1031 378/65 |
| 2012/0053961 A1* | 3/2012 | Wang | A61N 5/103 705/2 |
| 2012/0123184 A1* | 5/2012 | Otto | A61N 5/1067 600/1 |
| 2012/0136194 A1* | 5/2012 | Zhang | A61N 5/103 600/1 |
| 2012/0136677 A1* | 5/2012 | Ziegenhein | G06Q 50/22 705/2 |
| 2012/0203053 A1* | 8/2012 | Kilby | A61N 5/10 600/1 |
| 2012/0310615 A1* | 12/2012 | Moore | G06F 19/3481 703/11 |
| 2013/0131428 A1* | 5/2013 | Jiang | A61N 5/1031 600/1 |
| 2013/0197878 A1* | 8/2013 | Fiege | G06F 30/20 703/2 |
| 2013/0217948 A1* | 8/2013 | Mihaylov | A61N 5/1031 600/1 |
| 2013/0324784 A1* | 12/2013 | Fredriksson | A61N 5/103 600/1 |
| 2014/0171726 A1* | 6/2014 | Gum | A61N 5/1049 600/1 |
| 2014/0275710 A1 | 9/2014 | Zankowski | |
| 2014/0336438 A1* | 11/2014 | Bharat | A61N 5/1031 600/1 |
| 2014/0350322 A1* | 11/2014 | Schulte | A61N 5/1031 600/1 |
| 2014/0378736 A1* | 12/2014 | Fox | A61N 5/103 600/1 |
| 2015/0087879 A1* | 3/2015 | Nelms | A61B 6/5294 600/1 |
| 2015/0094519 A1* | 4/2015 | Kuusela | A61N 5/1039 600/1 |
| 2015/0095051 A1* | 4/2015 | Bharat | G06Q 50/22 705/2 |
| 2015/0141733 A1* | 5/2015 | Kumar | A61N 5/1031 600/1 |
| 2015/0248780 A1* | 9/2015 | Caridad | A61N 5/103 345/441 |
| 2015/0273238 A1* | 10/2015 | Kumar | G16H 20/40 600/1 |
| 2016/0008630 A1* | 1/2016 | Ranganathan | A61N 5/1036 600/1 |
| 2016/0016008 A1* | 1/2016 | Kelly | A61N 5/1083 600/1 |
| 2016/0030767 A1* | 2/2016 | Kumar | A61N 5/1031 600/1 |
| 2016/0059037 A1* | 3/2016 | Bender | A61N 5/1031 600/1 |
| 2016/0089549 A1* | 3/2016 | Ranganathan | A61N 5/1045 600/1 |
| 2016/0136455 A1* | 5/2016 | Bharat | A61N 5/1038 600/1 |
| 2016/0166855 A1* | 6/2016 | Kumar | A61N 5/1039 600/1 |
| 2017/0021194 A1* | 1/2017 | Nelms | A61N 5/1048 |
| 2017/0173365 A1* | 6/2017 | Bzdusek | G16H 50/30 |
| 2017/0259082 A1* | 9/2017 | Bzdusek | G06F 19/321 |
| 2018/0028837 A1* | 2/2018 | Schaetti | A61N 5/103 |
| 2018/0043184 A1* | 2/2018 | Wu | G16H 20/40 |
| 2018/0078783 A1* | 3/2018 | H rdemark | G16H 50/50 |
| 2018/0078785 A1* | 3/2018 | Ollila | A61N 5/1039 |
| 2018/0078786 A1* | 3/2018 | Vik | A61N 5/1036 |
| 2018/0078792 A1* | 3/2018 | Ollila | A61N 5/1031 |
| 2018/0111005 A1* | 4/2018 | Ranganathan | A61N 5/1045 |
| 2018/0154177 A1* | 6/2018 | Bzdusek | A61N 5/1039 |
| 2018/0185669 A1* | 7/2018 | Kuusela | A61N 5/1031 |

OTHER PUBLICATIONS

Pugachev, et al., "Pseudo Beam's-Eye-View as Applied to Beam Orientation Selection in Intensity-Modulated Radiation Therapy"; Int. J. Radiation Oncology Biol. Phys., vol. 51, No. 5, pp. 1361-1370, 2001.

Pugachev, et al., "Incorporating Prior Knowledge Into Beam Orientaton Optimization in IMRT"; Int. J. Radiation Oncology Biol. Phys., vol. 54, No. 5, pp. 1565-1574, 2002.

Ranganathan, et al., "SU-G-BRC-01: A Data-Driven Pre-Optimization Method for Prediction of Achievability of Clinical Objectives in IMRT"; Medical Physics (vol. 43, issue 6Part24, pp. 3627 ) Jun. 2016.

Wu, et al., "Using overlap volume histogram and IMRT plan data to guide and automate VMAT planning: A head-and-neck case study"; Med. Phys. 40 (2), Feb. 2013.

Simari, et al., "A Statistical Approach for Achievable Dose Querying in IMRT Planning"; Medical Physics (vol. 43, Issue 6Part24, pp. 3627), Jun. 2016.

\* cited by examiner

PRE-OPTIMIZATION METHOD FOR QUICK PREDICTION OF ACHIEVABILITY OF CLINICAL GOALS IN INTENSITY MODULATED RADIATION THERAPY

CROSS REFERENCE TO RELATED APPLICATIONS

This application is the U.S. National Phase application under 35 U.S.C. § 371 of International Application No. PCT/EP2017/054680, filed Mar. 1, 2017, published as WO 2017/153211 on Sep. 14, 2017, which claims the benefit of U.S. Provisional Patent Application No. 62/305,647 filed Mar. 9, 2016. These applications are hereby incorporated by reference herein.

FIELD

The following relates generally to the radiation therapy arts, intensity modulated radiation therapy (IMRT) arts, volumetric-modulated arc therapy (VMAT) arts, oncology treatment arts, and related arts.

BACKGROUND

In a typical intensity modulated radiation therapy (IMRT) implementation, a beam of high energy particles (e.g. electrons, photons, protons, ions) is generated by a linear particle accelerator (linac). The target volume (e.g. malignant tumor) of an oncology patient is disposed in the path of the radiation beam. To more precisely irradiate the target volume while limiting radiation exposure of neighboring organs at risk (OARs), a multi-leaf collimator (MLC) is used to block designed portions of the radiation beam to provide a radiation beam of a desired shape. The MLC segments the radiation beam into "beamlets" that can be turned on or off by pre-programmed movement of leaves of the MLC. For additional dosage control, multiple beam pulses can be applied, with each beam pulse at a chosen energy and beam shape obtained by adjusting the beam energy and suitably configuring the MLC.

In conventional IMRT, the radiation beam produced by the linac is at a fixed spatial position and orientation, and the patient is also held in a fixed position to ensure precise conformance of the radiation distribution with the target volume. Accordingly, once the IMRT geometry is determined (i.e. the position of the target volume and OARs relative to the beam), dosage distribution is obtained by modulation of the beam energy over successive beam pulses in conjunction with MLC beam shaping. Some newer IMRT techniques provide further degrees of freedom, such as Volumetric Modulated Arc Therapy (VMAT) which further incorporates rotation of the radiation beam to provide successive beam pulses at different beam angles or over a continuous arc. This provides further flexibility in tailoring the dose conformance to the target volume while limiting exposure of OARs and decreases delivery time.

The planning process for IMRT is complex, and is performed by specialized medical professionals such as an oncologist, physicist, and/or dosimetrist. Initially, the patient is imaged by a technique such as computed tomography (CT) or magnetic resonance (MR) imaging. The CT or MR image constitutes a large three-dimensional (3D) image dataset capturing the target volume, OARs, and any radiation absorbing structures that may intersect the radiation beam path. The target volume and neighboring OARs are delineated in the 3D image data set, usually by contouring individual image slices. Automated or semi-automated contouring may be used to assist this process, but the final contours must be approved by appropriate medical personnel. The target radiation dose distribution is also defined, for example in terms of desired radiation dosage in the target volume (or at specific locations in that volume) and permissible radiation dosage tolerances in each OAR. These dose distribution parameters are commonly referred to as the objective, or objectives, of the radiation therapy plan.

Computerized IMRT planning is then performed to determine a program of beam pulses and their beam energies and MLC configurations in order to achieve the desired dose distribution objectives. MLCs used in clinical radiation therapy can modulate hundreds or even thousands of beamlets, and additional adjustments can be made in the number of beam pulses and the beam energy of each pulse. Consequently, the number of variables to be optimized is very large (e.g. N beamlets where N may be greater than 1000, times the number of pulses). In some commonly used inverse planning approaches, a fluence map for each beam pulse is calculated such that the fluence maps computed for the beam pulses combine to produce the desired radiation dose distribution in the patient. In determining the dose distribution from the fluence maps, the spatially varying radiation absorption of different tissues of the patient must be accounted for—this is usually done using the 3D CT or MR image, with suitable transformation, as a radiation attenuation map. Each optimized fluence map is then discretized into a map of beamlets, and finally the MLC configuration to obtain each such map is determined. This is merely an illustrative example and other IMRT planning algorithms may be employed, e.g. working directly with the beamlets without computing intervening fluence maps, but it will be appreciated that any such planning algorithm is computationally intensive. In practice, several hours of computing time may be required to perform an IMRT plan optimization operating on the patient-specific dosage targets, contours, and attenuation map and outputting optimized MLC configurations.

The final optimized IMRT plan is usually not unique, even for a preselected radiation beam orientation, patient position, and number of beam pulses. Conversely, in some cases the desired dose distribution may be unobtainable, or may be unobtainable for given preselected settings (e.g. beam/patient orientation, number of pulses). In this case the plan optimization will fail to converge to an ideal solution. The dosimetrist may then try different initial conditions or modify the existing parameters and repeat the optimization process, and this cycle may be repeated several times before arriving at a realizable IMRT plan that satisfies the plan objectives specified by the patient's doctor. If the dosimetrist is unable to generate a realizable plan that satisfies these objectives after several such attempts, further consultation with the patient's doctor may be required in order to adjust the optimization objectives to be physically realizable while providing the intended therapeutic value.

The following discloses a new and improved systems and methods that address the above referenced issues, and others.

SUMMARY

In one disclosed aspect, a radiation therapy planning device comprises a computer including a display device, and at least one non-transitory storage medium that stores instructions readable and executable by the computer to perform operations including computing an achievability estimate for an intensity modulated radiation therapy (IMRT) geometry including a target volume to be irradiated, an organ at risk (OAR), and at least one radiation beam based on relative spatial arrangement of the target region, the OAR, and the at least one radiation beam, and displaying the achievability estimate or information generated based on the achievability estimate on the display device.

In another disclosed aspect, a non-transitory storage medium stores instructions readable and executable by a computer to perform a radiation therapy planning method comprising: computing an achievability estimate for an intensity modulated radiation therapy (IMRT) geometry including a target volume to be irradiated, an organ at risk (OAR), and at least one radiation beam based on comparison of a number $N_T$ of available beamlets of the at least one radiation beam that intersect the target volume and a number n of available beamlets of the at least one radiation beam that intersect both the target volume and the OAR; and displaying the achievability estimate or information generated based on the achievability estimate on a display of or operatively connected with the computer.

In another aspect, a radiation therapy planning method is disclosed. Using a computer, an achievability estimate is computed for an intensity modulated radiation therapy (IMRT) geometry including a target volume to be irradiated, an organ at risk (OAR), and at least one radiation beam. To this end, a geometric complexity (GC) metric is computed for the IMRT geometry that compares a number $N_T$ of beamlets of the at least one radiation beam available in the IMRT geometry for irradiating the target volume and a number n of the $N_T$ beamlets that also pass through the OAR. A GC metric ratio is then computed of (i) the GC metric for the IMRT geometry and (ii) the GC metric for a reference IMRT geometry for which an IMRT plan is known to be achievable. The achievability estimate is displayed on a computer display.

One advantage resides in reduction in wasted computing time due to failed IMRT plan optimization attempts.

Another advantage resides in providing faster IMRT planning Another advantage resides in providing semi-automated guidance for selecting parameters of an IMRT plan prior to initiating IMRT plan optimization.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

In approaches disclosed herein, prior to performing the computationally intensive intensity modulated radiation therapy (IMRT) plan optimization, the clinician (e.g. oncologist, dosimetrist, etc) is given an efficiently computed achievability estimate, which provides an estimate of the likelihood that an IMRT plan can be generated for the IMRT geometry chosen by the clinician.

More particularly, the achievability estimate is determined for an IMRT geometry that includes a target volume to be irradiated (typically a cancerous tumor but possibly some other malignant volume such as a highly metastasized region of an organ), an organ at risk (OAR) of damage due to undesired radiation exposure, and at least one radiation beam. The achievability estimate is computed based on relative spatial arrangement of the target region, the OAR, and the at least one radiation beam. In the illustrative embodiments, the achievability estimate is not based on any dose objectives for either the target volume or the OAR (the latter being typically a maximum permissible dose).

The disclosed approaches for providing an efficiently computed achievability estimate are founded on several observations made herein. One observation is that the inability to achieve an IMRT plan for a particular IMRT geometry is due to situations in which the radiation beam intersects both the target volume (as desired) and also the OAR (which is undesired). More particularly, in IMRT the multileaf collimator (MLC) defines available beamlets, and any beamlet that does not intersect the OAR does not contribute to inability to achieve a workable IMRT plan for the IMRT geometry. On the other hand, any beamlet that intersects both the target volume and the OAR can contribute to inability to achieve a workable IMRT plan for the IMRT geometry, because applying that beamlet during IMRT delivery contributes to irradiating the target volume, but also contributes to undesired irradiation of the OAR. If this undesired irradiation of the OAR is too high (above the maximum permissible dose as defined by the therapy dose objectives) for any possible MLC configuration, then it is not possible to optimize a workable IMRT plan using that IMRT geometry. Hence, the disclosed achievability estimate is computed based on comparison of a number $N_T$ of available beamlets of the (at least one) radiation beam that intersect the target volume and a number n of available beamlets of the (at least one) radiation beam that intersect both the target volume and the OAR. The number n is less than or equal to $N_T$, and in general the closer n becomes to $N_T$ the less likely it becomes that an IMRT plan can be optimized for the given IMRT geometry.

As used herein, the term "available beamlet" in the context of a given IMRT geometry refers to a beamlet of the radiation beam that, if not blocked by the MLC, will irradiate the target volume. In other words, "available beamlets" are those beamlets of the radiation beam modulated by the MLC that, if not blocked by the MLC, will intersect the target volume. Accordingly, the number of available beamlets is $N_T$. Note that if the radiation beam area is large enough that peripheral portions of the radiation beam do not intersect the target volume, than any beamlets in those peripheral portions are not "available" beamlets, because they cannot contribute to irradiating the target volume even if unblocked by the MLC.

The actual dose objectives also impact achievability of an IMRT plan for a given IMRT geometry. However, it is recognized herein that this impact can be approximated, for the purpose of providing an estimate of the likelihood of achieving an IMRT plan, without actually performing the IMRT plan optimization (which, as discussed previously, is computationally intensive). In illustrative achievability estimates disclosed herein, the impact of the dose objectives is accounted for in approximate fashion by comparing a "geometric complexity" or GC metric computed for the IMRT geometry based on relative spatial arrangement of the target region, the OAR, and the at least one radiation beam with the same GC metric computed for a reference IMRT geometry. The reference IMRT geometry is preferably chosen to be an IMRT geometry for an IMRT plan with dose objectives similar to those desired for the current therapy. The maximum permissible dose for an OAR is typically related to known damage thresholds for various organs, while the dose objective for the target volume is similarly related to known dosage levels for clinical efficacy for treating a given type of cancer.

In view of the foregoing, the illustrative achievability estimates are computed based on relative spatial arrangement of the target region, the OAR, and the at least one radiation beam, and not based on any dose objective. In illustrative example, the achievability estimate is computed using a "geometric complexity" or GC metric that compares (i) the number $N_T$ of available beamlets (i.e. those that intersect the target volume) and (ii) the number n of those available beamlets that also intersect the OAR. In some embodiments, the GC metric for the IMRT geometry is compared with the GC metric for a reference IMRT geometry known to enable at least one achievable IMRT plan (preferably with similar dose objectives compared with the IMRT plan under current development), so as to approximately account for the impact of the dose objectives.

Figure 1:
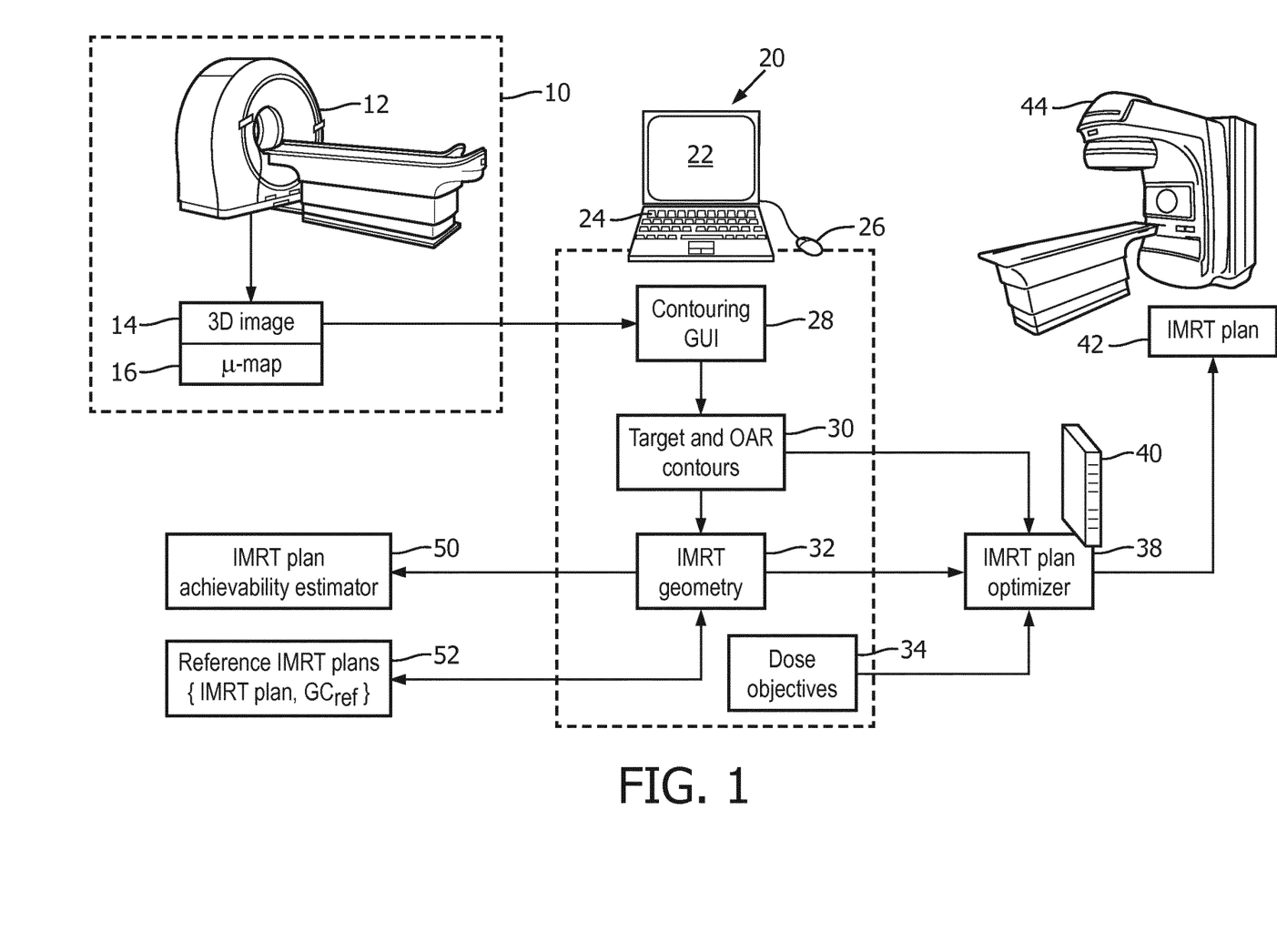
FIG. 1 diagrammatically shows an illustrative intensity modulated radiation therapy (IMRT) planning device in context with the imaging and radiation therapy delivery apparatuses.

With reference now to FIG. 1, an illustrative intensity modulated radiation therapy (IMRT) planning device is illustrated in context with the imaging and radiation therapy delivery apparatuses. The IMRT planning process begins with the patient being imaged at a radiology laboratory 10 using a suitable imaging device such as an illustrative computed tompography (CT) imaging device 12, a magnetic resonance (MR) imaging scanner, or so forth. The radiology laboratory 10 delivers a three-dimensional (3D) image 14 of the patient, or at least of the tumor or other IMRT target volume and neighboring organs at risk (OAR's). Commonly, the 3D image 14 is processed to generate an attenuation map 16 (or μ-map, sometimes also called an absorption map) which is used in the IMRT plan optimization to account for radiation absorption by various tissues of the oncology patient undergoing IMRT. For the illustrative 3D image 14 acquired by CT imaging, the attenuation map 16 is readily generated by converting the CT Hounsfield numbers to account for different absorption characteristics of the therapeutic radiation beam compared with the x-rays used for the CT imaging. Generating the attenuation map 16 from an MR image may be done, for example, by segmenting the image and assigning attenuation values to different segments of the segmented image.

The 3D image 14 serves as a planning image for planning the IMRT. To this end, the planning image 14 is contoured by a clinician (e.g. oncologist or dosimetrist) to define the target volume and any neighboring organs at risk (OARs) that may receive undesired radiation during the irradiation of the target volume. The contouring is typically a manual or semi-manual process performed by a clinician operating a user interfacing computer 20 having (or operatively connected with) a display 22 and one or more user input devices (e.g. a keyboard 24, mouse or other pointing device 26, touch-sensitive overlay of the display 22, and/or so forth). The computer 20 is programmed to provide a contouring graphical user interface (GUI) 28 via which the user can draw contours in slices of the 3D planning image 14 delineating the target volume and OARs. Additionally or alternatively, automated or semi-automated contouring may be provided, e.g. defining a contour as meshes surrounding the target volume and OARs with each mesh defined to include the points identified by the clinician during manual contouring and possibly also delineated by fitting the mesh to edges of objects identified by image gradients or the like.

The output of the contouring performed via the contouring GUI 28 (optionally with the assistance of semi-automated contouring; fully automated contouring is also contemplated, with review/approval of the clinician) is a set of contours 30 delineating the target volume and any OAR whose (undesired) irradiation is to be controlled. The clinician completes the IMRT geometry 32, which includes the target volume and OAR defined by the contours 30, by also choosing the orientation of the radiation beam (or radiation beams, if the IMRT delivery device can output multiple radiation beams simultaneously and/or at different times). The spatial location of the radiation beam respective to the target volume and the OARs is determined based on practical constraints (e.g., the patient is usually lying in a prone, i.e. face-down, or supine, i.e. face up, position), the need to position the target volume at or near the center of the radiation beam, and the desire to limit exposure of OARs. Thus, the IMRT geometry 32 includes the target volume to be irradiated, at least one organ at risk (OAR), and at least one radiation beam. A further input from the clinician for designing the IMRT plan is the dose objectives 34. Typically, these may include a minimum (and/or target) radiation dose to be delivered to the target volume, and a maximum permissible dose for each OAR. Each OAR may, in general, have a different maximum permissible dose depending upon radiation sensitivity of the particular organ. Some of the dose objectives 34 may be formulated as hard or soft constraints; e.g. the maximum permissible dose for a life-critical OAR may be a hard constraint to ensure safety of the patient.

Conventionally, with the IMRT geometry 32 and dose objectives 34 set, the IMRT planning would proceed to IMRT plan optimization performed by an IMRT plan optimizer 38, implemented on a suitably powerful computer 40 such as a network server computer, a cloud computing resource or other distributed computing system, or so forth. The IMRT plan optimization computer 40 may optionally employ specialized components (e.g. an ASIC) to perform some optimization operations. By way of non-limiting illustration, the IMRT plan optimizer 38 may employ an inverse planning approach in which a fluence map for the radiation beam is optimized to produce the desired dose objectives, using the attenuation map 16 to determine the radiation profile, and the resulting fluence map then discretized to generate the MLC configuration. The resulting IMRT plan 42 is stored in a non-transitory data storage and, at the scheduled time, the patient undergoes IMRT delivery performed using a radiation therapy delivery apparatus 44, e.g. comprising a linac to generate the radiation beam and an MLC to modulate the beam in accord with the IMRT plan 42.

It may be noted that in illustrative FIG. 1, the computer 20 implementing the contouring GUI 28 and the user interfacing for selection of the overall IMRT geometry 32 and the dose objectives 34 is separate from the computer 40 that is programmed to implement the IMRT plan optimizer 38. This is a common arrangement since the user interfacing computer 20 requires user interfacing components 22, 24, 26 and preferably includes features supporting the contouring such as an optional graphical processing unit (GPU) or other graphics acceleration hardware and so forth; whereas, the IMRT plan optimizer 38 is preferably implemented on a high-capacity computer or computing network or cloud computing resource providing sufficient computing power. However, it is contemplated for a single computer to implement or support both the user interfacing aspects 28, 30, 32, 34 and the IMRT plan optimizer 38. For example, another suitable implementation is a network server computer or computer cluster (e.g., a server or servers on a hospital electronic network) and one or more "dumb" terminals or personal computers connected with the network server computer(s)—in this implementation, the user interfacing components of the terminal or personal computer provide for the contouring and so forth, while the optimization is performed on the network server computer(s) with the results displayed on the terminal or personal computer.

As previously noted, the IMRT plan optimization entails hundreds or thousands of parameters to be optimized, and may take several hours of computing time. Depending upon the choice of IMRT geometry 32 and dose objectives 34, the IMRT plan optimization may fail to converge to a physically realizable solution—in this case the clinician must return to the planning stage by updating the IMRT geometry 32 and/or the dose objectives 34, or in some cases may even need to go back to the contouring GUI 28 to update the target volume and/or OAR contours. Such a circumstance wastes valuable computing resources and clinician time, and may delay time-critical delivery of radiation therapy to the patient.

To alleviate these potential problems, the illustrative IMRT planning device of FIG. 1 further includes an IMRT plan achievability estimator 50, which may be variously implemented on the user interfacing computer 20, or the IMRT optimization computer 40, or on a combined computer performing both functions, or so forth. The IMRT plan achievability estimator 50 estimates likelihood that a physically realizable IMRT plan can be generated by the IMRT plan optimizer 38 for the chosen IMRT geometry 32. This estimation is done based on the IMRT geometry 32 (including the target volume and OAR definitions and the chosen radiation beam(s)), but in the illustrative embodiments does not rely upon the dose objectives 34. Rather, in illustrative embodiments the user selects, from a reference IMRT plans database 52, an IMRT plan with a similar IMRT geometry and (preferably) similar dose objectives, and a geometric complexity (GC) metric is computed for the chosen IMRT geometry 32 and for the IMRT geometry of the reference IMRT plan. Based on comparison of the GC metric and the reference GC metric, the achievability is estimated. In general, if the GC metric of the chosen IMRT geometry 32 is significantly higher than the reference GC metric, this indicates that chosen IMRT geometry 32 presents a significantly more geometrically complex situation making it less likely that an IMRT plan can be successfully optimized for the geometrically complex IMRT geometry. The resulting IMRT plan achievability estimate is suitably displayed on the display 22. The display may be a numeric value, or may be translated to a textual achievability estimate value such as "Achievable", "Possibly achievable", "Probably not achievable", or "Not achievable" by binning the numerical achievability estimate and selecting the textual achievability estimate value based on the binned numerical estimate.

It should be noted that the achievability estimate is intended as guidance for the clinician as to whether it is advisable to proceed with the IMRT plan optimization for the chosen IMRT geometry 32. Because of this, the achievability estimate can have a significant level of error, i.e. in some cases the achievability estimate may indicate an IMRT plan optimization is achievable when in actuality it turns out the IMRT plan optimizer 38 is unable to generate a physically realizable plan; or vice versa. The IMRT plan achievability estimator 50 serves a useful purpose if it is usually accurate, i.e. if usually when it predicts an IMRT plan is achievable it is correct, and if usually when it predicts an IMRT plan is not achievable this is correct. This is sufficient for the IMRT plan achievability estimator 50 to significantly reduce wasted optimization computing time and clinician time.

Having provided an overview of the IMRT planning device, which includes the IMRT plan achievability estimator 50, with reference to FIG. 1, in the following some illustrative examples of some suitable IMRT plan achievability estimations are provided. The illustrative IMRT plan achievability estimators in general operate based on comparison of (i) a number $N_T$ of available beamlets of the at least one radiation beam that intersect the target volume and (ii) a number n of available beamlets of the at least one radiation beam that intersect both the target volume and the OAR. More particularly, a geometric complexity (GC) metric is defined as follows:

$$GC = \frac{n+1}{N_T/V} = \frac{n+1}{N} \quad (1)$$

where V is the volume of the target volume (e.g. the volume of the tumor to be irradiated) and $N=N_T/V$ is the number of available beamlets per unit volume of the target volume. It will be appreciated that other similar GC metrics could be used, e.g. in some embodiments no normalization is employed (yielding $GC=(n+1)/N_T$). The "+1" in Equation (1) reduces certain possible division-by-zero scenarios, but is in general optional (e.g., GC=n/N is contemplated).

Figure 2:
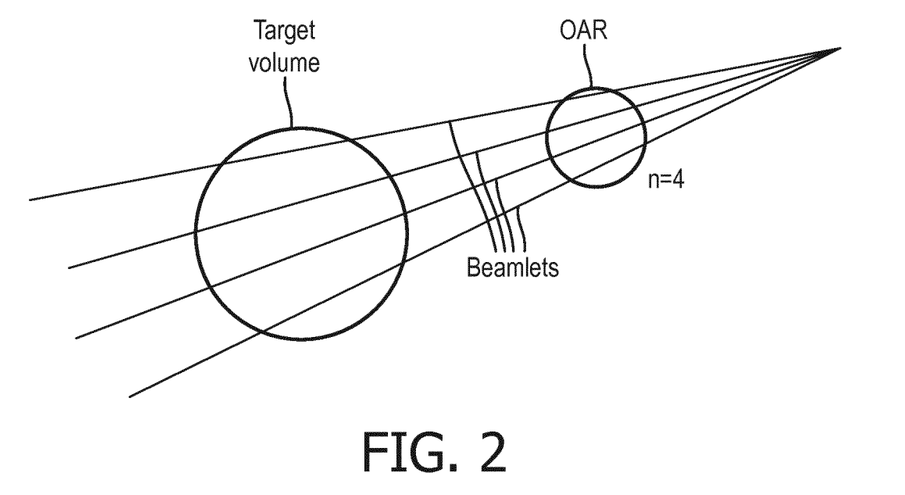
FIGS. 2-6 diagrammatically illustrate examples of disclosed achievability estimation approaches disclosed herein.
Figure 3:
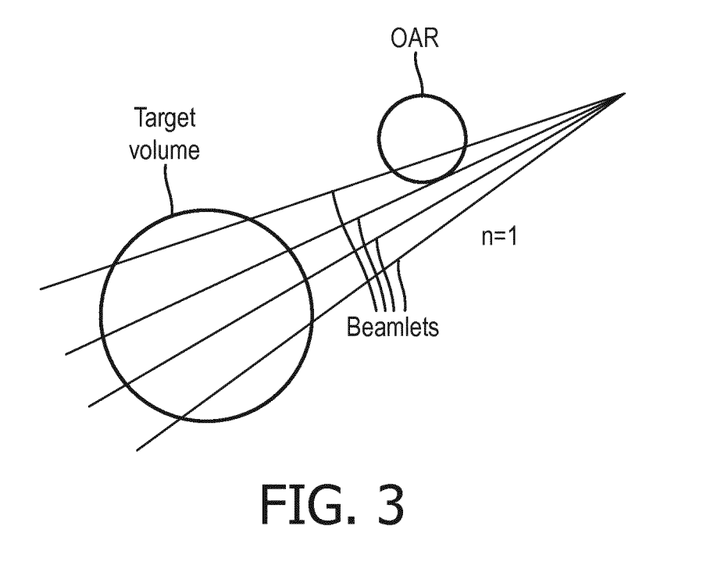

With reference to FIGS. 2 and 3, two illustrative examples of the efficacy of Equation (1) for estimating achievability are shown. FIGS. 2 and 3 diagrammatically illustrate two examples of a target volume and an OAR being irradiated by a single radiation beam. In this example, the number $N_T$ of available beamlets is four. (This is diagrammatic: as already noted, in practical IMRT implementations $N_T$ is typically on the order of hundreds or thousands). In the example of FIG. 2, all four available beamlets pass that intersect the target volume also intersect the OAR, so that n=4. This results in a high value for the GC metric of Equation (1), indicating high geometrical complexity and a low likelihood of achieving a successful IMRT plan optimization. By comparison, FIG. 3 shows a different IMRT geometry in which only one of the beamlets that intersect the target volume also intersects the OAR, leading to n=1. This results in a low value for the GC metric of Equation (1), indicating low geometrical complexity and a high likelihood of achieving successful IMRT plan optimization. (For example, that single beamlet intersecting the OAR could be shuttered off by the optimized MLC configuration).

Figure 4:
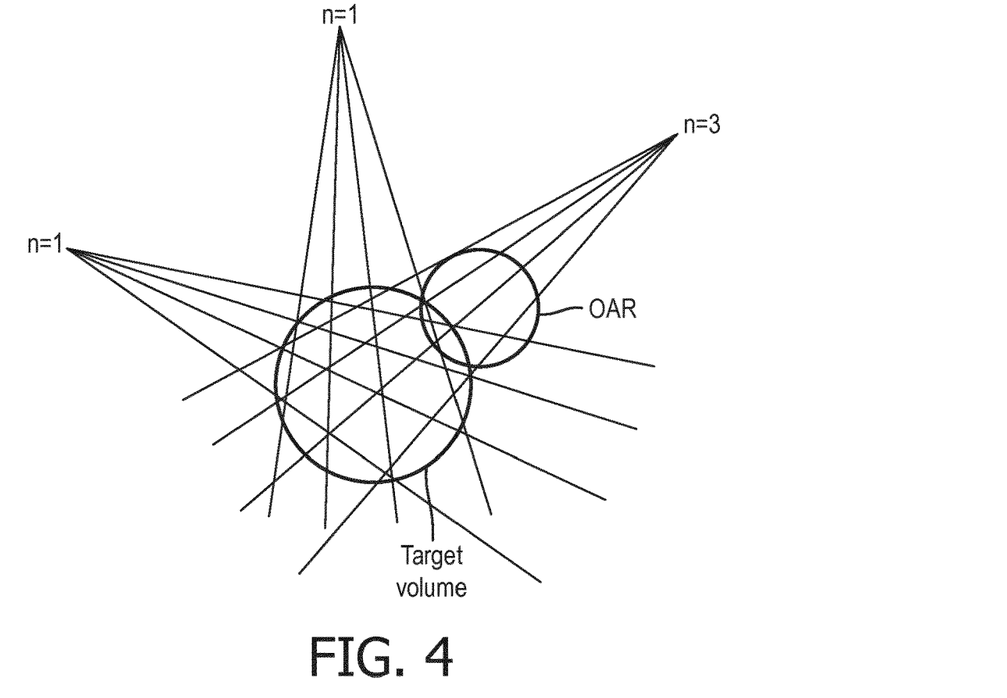

With reference to FIGS. 4 and 5, an example with three radiation beams is shown. In general, the three radiation beams may be applied simultaneously, or at successive time intervals, e.g. in accord with a volumetric-modulated arc therapy (VMAT) approach. (Since it is typically the time-integrated dose delivered in a single radiation therapy session to the target volume and OARs that is of importance, the time interval between successive radiation beam pulses is not relevant and the successive radiation beam pulses can be viewed as separate radiation beams). In this example, each radiation beam is modulated into four beamlets (again, a simplistic diagrammatic example), so that for the three radiation beams $N_T=4\times3=12$. In the example of FIG. 4, one beamlet of the leftmost radiation beam also intersects the OAR, one beamlet of the middle radiation beam also intersects the OAR, and three beamlets of the rightmost radiation beam also intersect the OAR. Thus, n=1+1+3=5, and from Equation (1) the GC metric is $$\left(\frac{6}{12}\right)V.$$

Figure 5:
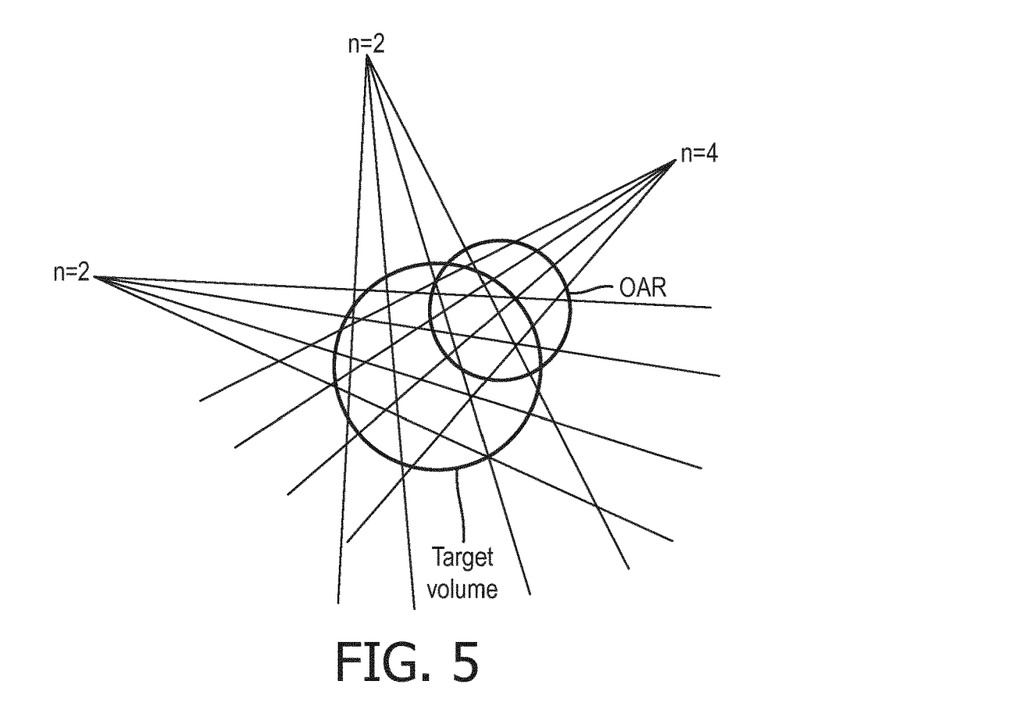

In the example of FIG. 5, two beamlets of the leftmost radiation beam also intersects the OAR, two beamlets of the middle radiation beam also intersects the OAR, and all four beamlets of the rightmost radiation beam also intersect the OAR. Thus, n=2+2+4=8, and from Equation (1) the GC metric is $$\left(\frac{9}{12}\right)V.$$

It follows that the IMRT geometry of FIG. 4 is more likely to yield an achievable IMRT plan optimization (because of its lower GC) as compared with the IMRT geometry of FIG. 5 (because of its higher GC).

Figure 6:
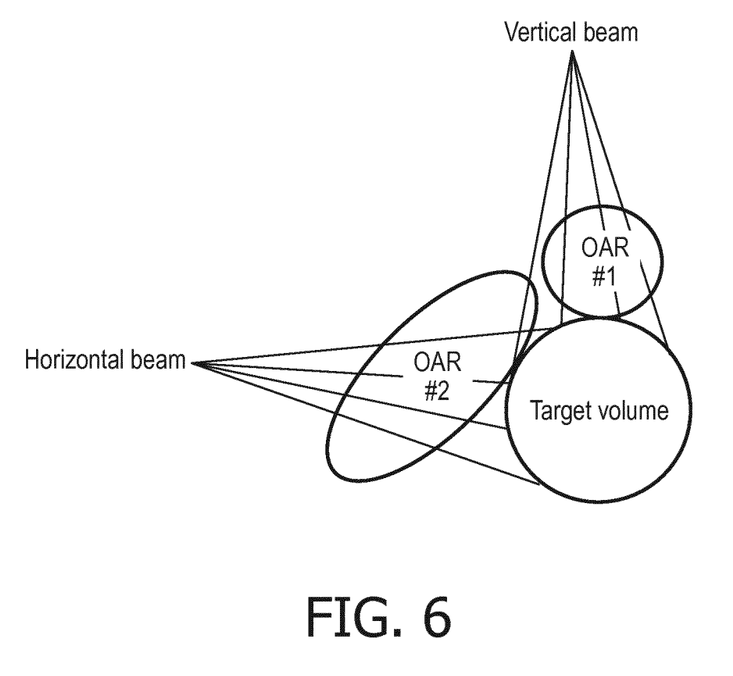

With reference to FIG. 6, if there are two or more OARs this can be handled in various ways. Illustrative FIG. 6 shows two OARs denoted as "OAR #1" and "OAR #2", respectively, along with two radiation beams. The horizontal radiation beam has four beamlets intersecting OAR #2 with none intersecting OAR #1. The vertical radiation beam has three beamlets intersecting OAR #1 and one beamlet intersecting OAR #2. In one approach, the two OARs are treated as a single OAR, i.e. there is a single OAR which is the union of the individual OARS (e.g. here the single OAR is {OAR #1 U OAR #2}. In this case, n=8 (since every beamlet intersects at least one of the constituent OARs) and $N_T=8$, so that the GC metric is $$\left(\frac{9}{8}\right)V.$$

The very high value of the GC metric indicates low likelihood of achieving an optimized IMRT plan with this IMRT geometry. This is useful information, but does not inform the clinician as to which OAR is most significantly lowering the likelihood of successful plan optimization.

In another approach, each OAR is treated separately: in this case, the GC metric for OAR #1 is $$\left(\frac{4}{8}\right)V$$

and the GC metric for OAR #2 is $$\left(\frac{6}{8}\right)V.$$

The clinician is thus informed that OAR #2 is more significantly lowering the likelihood of successful plan optimization as compared with OAR #1. However, in this approach the individual GC metric values may strongly overestimate the likelihood of achieving an optimized IMRT plan—in the example of FIG. 6, each individual GC metric is significantly lower than the GC metric when considering both OARs, thus overestimating the likelihood of achieving an optimized IMRT plan. In one approach, the "total" GC metric treating both OARs together and having value in this instance of $$\left(\frac{9}{8}\right)V$$

is displayed (thus indicating a very low achievability likelihood), and additionally the GC metric for each OAR is also displayed to provide assistance in determining which OAR(s) adversely impact achievability. (In similar fashion, the GC metric for each individual radiation beam could be displayed to indicate which beam or beams is adversely impacting achievability of an optimized IMRT plan).

In some contemplated embodiments, the GC metric of Equation (1), or a variant such as one of the variants described herein which omits the "+1" term and/or omits the volume (V) normalization, is used as the achievability estimate. It can be seen from the examples of FIGS. 2-5 that as GC increases, the number n of beamlets that intersect both the target volume and the OAR increases, reflecting greater geometric complexity and consequent lower likelihood of successful IMRT plan optimization. However, relying upon GC directly as the achievability estimate does not provide any mechanism for considering the impact of the dose objectives 34, as Equation (1) is a purely geometrical analysis. In practice, the dose objectives 34 will also impact whether an IMRT plan can be successfully optimized. For example, as the maximum permissible dose to the OAR is reduced (as compared with the intended dose for the target volume), it becomes more difficult to achieve an optimized IMRT plan satisfying that lowered maximum permissible OAR dose. Conversely, as the maximum permissible dose to the OAR is increased it becomes easier to achieve an optimized IMRT plan since more radiation dose can be absorbed by the OAR. But computing the doses delivered to the target volume and the OAR would entail performing the IMRT plan optimization, which would defeat the goal of performing an initial achievability estimate before performing the computationally complex IMRT plan optimization.

In illustrative embodiments, instead of basing the achievability estimate on any of the dose objectives 34, this information is semi-quantitatively taken into account by comparing the GC metric computed via Equation (1) for the IMRT geometry 32 under consideration with a reference GC metric computed, again via Equation (1), for a reference IMRT geometry of an IMRT plan that was actually optimized. Hence, the reference IMRT geometry is known to enable successful optimization of an IMRT plan (since this has been done for the reference IMRT geometry in the past). The reference IMRT plan chosen from the reference IMRT plans database 52 is preferably chosen to be as close as possible to the IMRT plan to be developed—in particular, the reference IMRT plan should have the same or similar IMRT geometry to the chosen IMRT geometry 32, and the dose objectives of the reference IMRT plan should be close to the dose objectives 34 of the IMRT plan to be developed.

The reference IMRT plan may be selected manually, e.g. by having the clinician browse past IMRT plans stored in the database 52, or may be selected automatically, e.g. by closest match of the IMRT geometry and dose objectives, or by a combination thereof, e.g. automatically selecting those past IMRT plans for the same OAR and the same type of radiation therapy (e.g. same type of cancerous tumor) and having the clinician browse this sub-set of past IMRT plans for the closest plan. Moreover, in embodiments in which the achievability estimate is computed for each OAR separately, as discussed with reference to FIG. 6, it is contemplated to employ a different reference IMRT plan for estimating the achievability for each OAR. (This could also be extended to the case in which two or more target volumes are to be irradiated; achievability of each OAR/target volume combination can be estimated separately using a reference IMRT plan chosen for the OAR/target volume combination). The GC metric for the chosen reference IMRT plan is suitably computed as:

$$GC_{ref} = \frac{n_{ref} + 1}{N_{T,ref} / V_{ref}} = \frac{n_{ref} + 1}{N_{ref}} \quad (2)$$

where Equation (2) is identical with Equation (1) except for use of the subscript-ref to indicate values for the reference IMRT plan geometry. The achievability estimation is then based on the GC-ratio:

$$GC_{ratio} = \frac{GC}{GC_{ref}} = \frac{\left(\frac{n+1}{N}\right)}{\left(\frac{n_{ref}+1}{N_{ref}}\right)} \quad (3)$$

In the achievability estimate formulation of Equation (3), the volume normalization ($N=N_T/V$) is useful to approximately account for differences in tumor size when comparing the IMRT plan to be developed with the reference IMRT plan. Again, this is optional, especially if the database 52 is large enough that the clinician can usually select a reference IMRT plan for a similarly sized tumor. The optional "+1" factor is also seen to avoid the possibility of division-by-zero in the case of $n_{ref}=0$. The $GC_{ratio}$ of Equation (3) approximately takes into account the dose objectives since a $GC_{ratio}$ of about unity corresponds to the reference IMRT geometry which was known to be achievable. However, the achievability estimation of Equation (3) is not based on any dose objective (and hence does not require performing the computationally intensive dose optimization), but rather is based on the IMRT geometry 32 and the reference IMRT plan and its $GC_{ref}$ value.

In some embodiments, the achievability estimate is the quantitative value, e.g. the GC metric of Equation (1) if no reference is used, or the $GC_{ratio}$ of Equation (3) if the reference IMRT plan is used. However, these numerical values may not be intuitive for the clinician, especially since in both cases a higher value corresponds to lower likelihood of achievability which might be seen as counterintuitive. In illustrative embodiments, the $GC_{ratio}$ is binned and a look-up table, shown as Table 1 herein, is used to convert the numerical value to a textual achievability estimate value that has manifest semantic meaning. It is to be understood that the quantitative values in illustrative Table 1 are representative, and that specific values for the $GC_{ratio}$ bins may be chosen for specific types of IMRT planning and for the general IMRT geometric layout. It should also be noted that due to the achievability estimate being an estimate, the category of "Achievable" does not imply certainty that an IMRT plan can be optimized for a geometry having an "Achievable" estimate, but rather indicates a high likelihood that such a plan will be achievable; likewise, "Not achievable" does not conclusively mean that an IMRT plan cannot be optimized with the geometry, but only that such optimization is highly unlikely.

TABLE 1

Interpretation of $GC_{ratio}$

| $GC_{ratio}$ | textual achievability estimate value | Abbreviation |
|---|---|---|
| >1.3 | "Not achievable" | NA |
| 1.2 to 1.3 | "Probably not achievable" | PNA |
| 1.0 to 1.2 | "Possibly achievable" | PA |
| <1.0 | "Achievable" | A |

The achievability estimation of Equation (3) with the interpretation of Table 1 was applied to estimate achievability with respect to an OAR consisting of the right parotid duct in the context of head-and-neck IMRT planning. The experiments were carried out as follows. A reference Head and Neck plan was first created in which all the clinical objectives have been met through optimization. The $GC_{ref}$ metric associated with each segmented clinical structure (OAR) was extracted for the reference plan. The GC metric was computed for the right parotid duct OAR for other Head and Neck cases and these GC metric values were compared against the respective reference $GC_{ref}$ values obtained in the reference case. The geometric complexity ratio ($GC_{ratio}$) of Equation (3) was then computed, and the value converted to a textual achievability estimate value using Table 1. In the IMRT geometries, seven equiangular beams at: 0°, 50°, 100°, 150°, 200°, 250°, and 300°, were used in all cases. The achievability estimate of Equation (3) and Table 1 correctly predicted the IMRT plan optimization result about 85% of the time. This is sufficient for the disclosed achievability estimator to significantly reduce wasted computational and clinician time by avoiding performing IMRT plan optimizations that are likely to fail to succeed.

Figure 7:
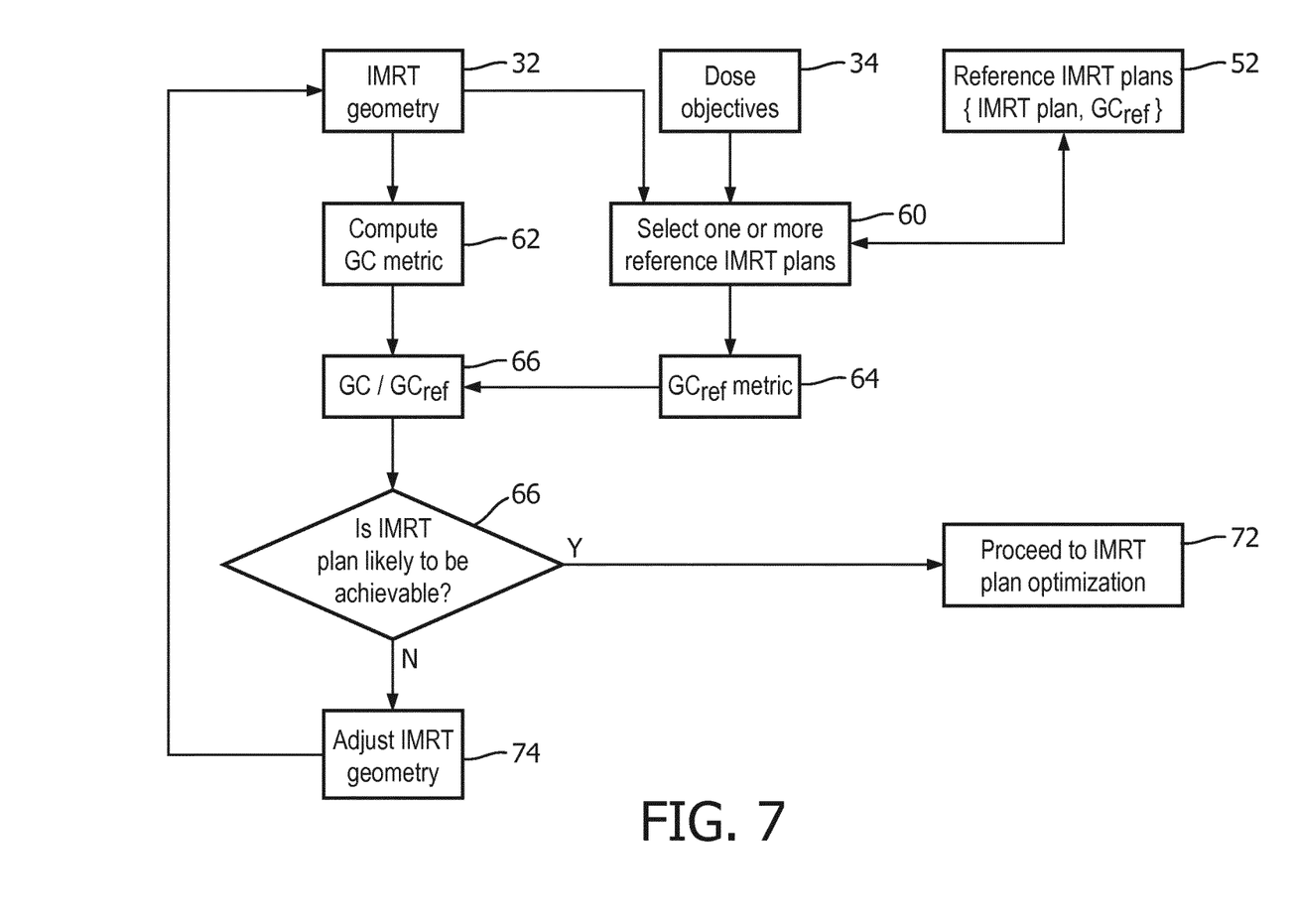
FIGS. 7 and 8 diagrammatically show two illustrative IMRT planning methods that may be suitably implemented using the IMRT planning device of FIG. 1.

With reference to FIG. 7, an IMRT plan optimization achievability estimation method suitably performed using the IMRT planning device of FIG. 1 is shown. In an operation 60 the reference IMRT plan is selected from the reference IMRT plans database 52. This may be done manually by the clinician by browsing the past IMRT plans to find a plan that is similar in terms of the IMRT geometry 32 and the dose objectives 34, or may be done automatically or semi-automatically by a computer search of the database 52. In an operation 62 the GC metric is computed for the IMRT geometry 32, for example in accord with Equation (1). In an operation 64 the $GC_{ref}$ metric is computed for the IMRT geometry of the reference IMRT plan, for example in accord with Equation (2). In some embodiments the operation 64 is performed offline for all past IMRT plans in the database 52 and stored as {IMRT plan, $GC_{ref}$} data pairs. In an operation 66, the $GC_{ratio}$ is computed, for example in accord with Equation (3). Optionally, this is converted to a textual achievability estimate value, for example using Table 1. In an operation 70 the clinician reviews the achievability estimate and decides whether an IMRT plan optimization is likely to be achievable. This decision may take into account factors other than the achievability prediction, such as availability of computer time (e.g., if the workload on the computer 40 is low then a lower-likelihood IMRT geometry may be pursued). If the decision 70 is affirmative then in an operation 72 the IMRT plan optimizer 38 is invoked to attempt to generate an optimized IMRT plan. If the decision 70 is negative then in an operation 74 the clinician adjusts the IMRT geometry (e.g., modifies the radiation beam angle, and if necessary may adjust the contours) and may try again.

In another aspect, the disclosed approach can be used to optimize the IMRT geometry prior to performing the IMRT plan optimization. One can infer from the GC metric that an IMRT geometry (e.g. the beam angle or position) suitable for a particular case may not be suitable for a different case. Since the GC metric is based on the IMRT geometry including the beam configuration respective to the target volume and the OAR(s), it is possible to formulate a radiation beam configuration selection problem using the GC metric, which can be solved using an iterative solver. In the following illustrative example, the beam configuration is chosen based on a combination beam angle, collimator angle and couch angle. Consider, for instance, the $GC_{ratio}$ obtained for different OARs, treating each OAR separately as previously discussed with reference to FIG. 6. The optimization may be formulated as:

$$F = \phi(W_1)(1-GC_{ratio}^{(OAR\#1)})^2 + \phi(W_2)(1-GC_{ratio}^{(OAR\#2)})^2 + \ldots + \phi(W_K)(1-GC_{ratio}^{(OAR\#K)})^2 \quad (4)$$

where F is the objective function to be minimized, $GC_{ratio}^{(OAR\ \#k)}$ is the $GC_{ratio}$ from Equation (3) rat for each OAR where k=1, ..., K, and $W_k$, k=1, ..., K is a weight for each OAR indicating the importance assigned to the $k^{th}$ OAR. In general, a larger value for $W_k$ indicates greater importance for keeping the irradiation of OAR #k below its maximum permissible dose. The function $\phi(W_k)$ is a binary selection function:

$$\phi(W_k) = \begin{cases} 0, & \text{if } GC_{ratio}^{(OAR\#k)} \leq 1 \\ W_k, & \text{if } GC_{ratio}^{(OAR\#k)} > 1 \end{cases} \quad (5)$$

An iterative solver can be used to minimize F, which will iteratively fine-tune the radiation beam configuration such that the cumulative $GC_{ratio}$ (i.e. the sum of ratios for all OARs in the IMRT plan) is as low as possible. By minimizing F, it is ensured that the radiation beam configuration is optimal to a given IMRT task with respect to the reference IMRT plan used to compute the $GC_{ratio}$ values.

In the foregoing examples, the reference IMRT plan is chosen by the clinician based on similarity with the IMRT plan (geometry and dose objective) currently under development. In other embodiments, the GC metric is computed for the IMRT plan under development, and this GC metric is used to automatically search the reference IMRT plans database 52 to identify a reference IMRT plan (or two, three, or several reference IMRT plans) with similar GC (i.e., having $GC_{ref}$ close to the GC computed for the IMRT plan under development). In this approach, only the geometry 32 of the IMRT plan under development is needed as an input in order to compute GC, and the dose objectives of the identified reference IMRT plans can then be used as guidance to the clinician in designing dose objectives 34 that are likely to be achievable.

Figure 8:
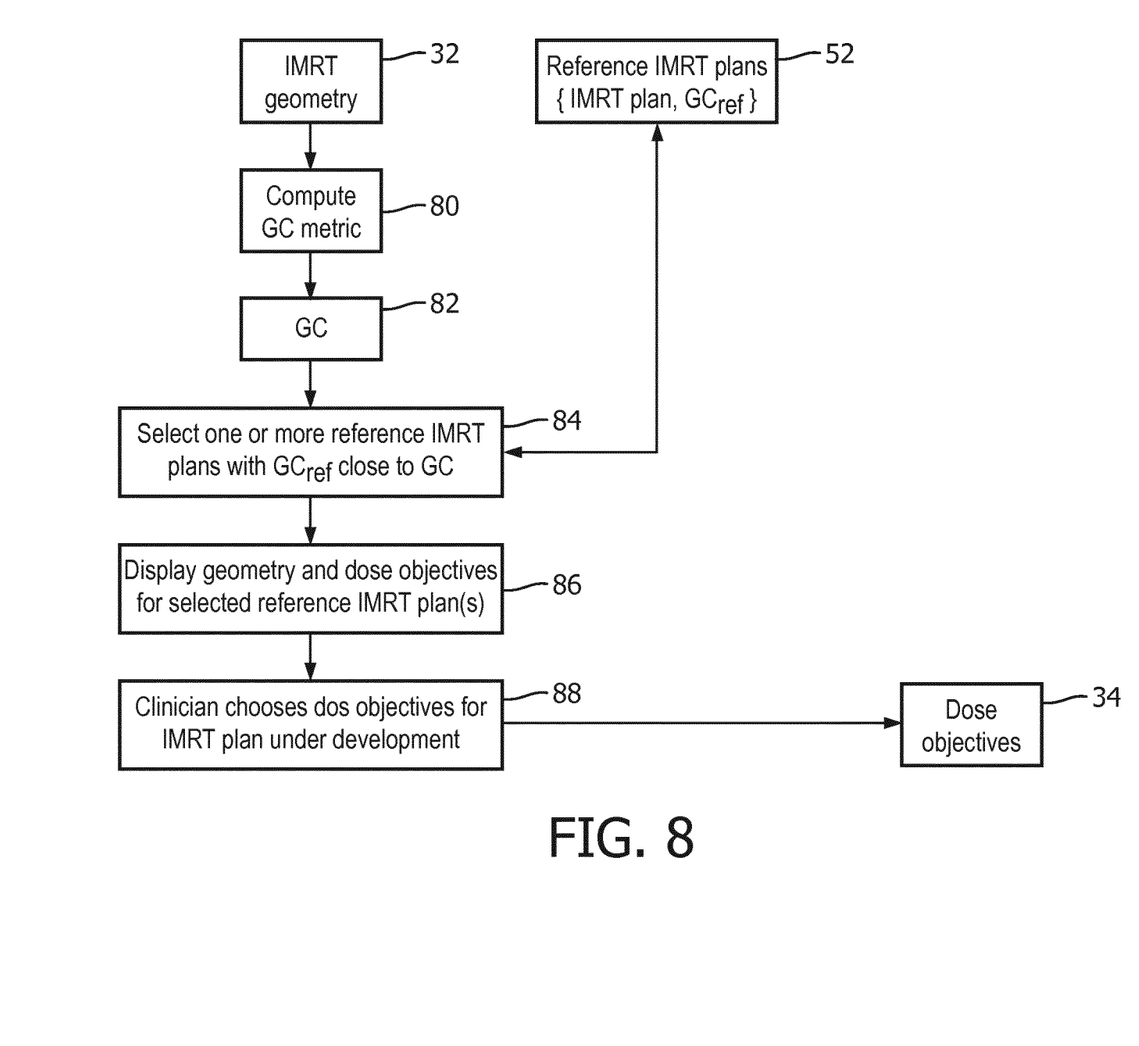

With reference to FIG. 8, an IMRT plan optimization achievability estimation method employing this alternative approach is shown. In an operation 80 the GC metric 82 is computed for the IMRT geometry 32, for example in accord with Equation (1). In an operation 84 the reference IMRT plans database 52 is searched to identify one or more references IMRT plans whose $GC_{ref}$ metric is most similar to the GC metric 82 computed for the IMRT plan geometry 32 intended for the IMRT plan under development. This search 84 is preferably automated, and is fast since it merely compares GC 84 against each $GC_{ref}$ stored in the database 52. (This assumes that the $GC_{ref}$ values are pre-calculated offline and stored in the database 52, which is preferred in this embodiment; alternatively, the $GC_{ref}$ metrics could be computed for each potential reference IMRT plan in the database 52, but this would then need to be re-done each time the method of FIG. 8 is executed for a new IMRT plan under development). Various criteria can be used for selecting the reference IMRT plan(s), such as selecting up to N plans whose $GC_{ref}$ is sufficiently close to GC 82 as measured by a suitable closeness metric, e.g. percent difference. The value of N could be as low as one (in which case a single closest reference IMRT plan is select) or could be higher, e.g. if N=5 then up to five closest reference IMRT plans are chosen. In an operation 86, information on the closest reference IMRT plans is displayed. This information may include, for example, the geometry, the dose objectives, information on patient outcome (if available), and/or so forth. The clinician is thus provided with salient information for a set of one or more similar reference IMRT plans, which may, for example, be referenced by the clinician in a manual operation 88 in which the clinician chooses the dose objectives 34 for the IMRT plan under development.

As previously discussed, the disclosed IMRT planning operations are suitably implemented by one or more computers 20, 40 executing instructions (e.g. a program) stored on at least one non-transitory storage medium. The at least one non-transitory storage medium may, for example, include one or more of: a hard drive or other magnetic storage medium; an optical disk or other optical storage medium; a flash memory or other solid-state electronic memory; various combinations thereof; or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:
1. A radiation therapy planning device comprising:
a computer including a display device; and
at least one non-transitory storage medium storing instructions readable and executable by the computer to perform operations including:
computing an achievability estimate for an intensity modulated radiation therapy (IMRT) geometry, wherein the IMRT geometry for which the achievability estimate is computed includes a relative spatial arrangement of a target volume to be irradiated, an organ at risk (OAR), and at least one radiation beam, and wherein the achievability estimate is computed based on relative spatial arrangement of the target region, the OAR, and the at least one radiation beam; and
displaying, on the display device, the achievability estimate or information generated based on the achievability estimate;
wherein the achievability estimate is computed based on any dose objective.

2. The radiation therapy planning device of claim 1 wherein the computing comprises:
computing the achievability estimate using a geometric complexity (GC) metric for the IMRT geometry that compares (i) a number $N_T$ of beamlets of the at least one radiation beam available in the IMRT geometry for irradiating the target volume and (ii) a number n of the $N_T$ beamlets that also pass through the OAR.

3. The radiation therapy planning device of claim 2 wherein the GC metric is a ratio comparing n and $N=N_T/V$ where V is the volume of the target volume.

4. The radiation therapy planning device of claim 3 wherein the GC metric is the ratio $$\frac{n+1}{N}.$$

5. The radiation therapy planning device of claim 2 wherein the achievability estimate comprises a ratio of the GC metric for the IMRT geometry and the GC metric for a reference IMRT geometry.

6. The radiation therapy planning device of claim 2 wherein:
the operations further include selecting at least one reference IMRT plan by comparing the CG metric for the IMRT geometry with GC metrics ($GC_{ref}$) computed for IMRT plans stored in a reference IMRT plans database; and
the displaying includes displaying information about the selected at least one reference IMRT plan including at least dose objectives of the at least one IMRT plan.

7. The radiation therapy planning device of claim 2 wherein computing the achievability estimate further includes determining a textual achievability estimate value based at least on the GC metric for the IMRT geometry the displaying comprising displaying the textual achievability estimate value on the display.

8. The radiation therapy planning device of claim 1 wherein the at least one non-transitory storage medium stores further instructions readable and executable by the computer to perform optimization of an IMRT plan for the IMRT geometry to select at least one multileaf collimator (MLC) configuration for modulating the beamlets of the at least one radiation beam to achieve pre-defined dose objectives using the IMRT geometry wherein the pre-defined dose objectives include at least a dose objective for the target volume and a maximum permissible dose objective for the OAR.

9. The radiation therapy planning device of claim 1 wherein the operations further include:
optimizing an objective function comprising a weighted sum of achievability estimates computed for IMRT geometries each including the same target volume and the same at least one radiation beam and each including a different OAR; and
adjusting one or more geometrical parameters of the at least one radiation beam to optimize the objective function.

10. A non-transitory storage medium storing instructions readable and executable by a computer to perform a radiation therapy planning method comprising:
computing an achievability estimate for an intensity modulated radiation therapy (IMRT) geometry, wherein the IMRT geometry for which the achievability estimate is computed includes a target volume to be irradiated, an organ at risk (OAR), and at least one radiation beam, the achievability estimate being computed based on comparison of a number $N_T$ of available beamlets of the at least one radiation beam that intersect the target volume and a number n of available beamlets of the at least one radiation beam that intersect both the target volume and the OAR; and
displaying the achievability estimate or information generated based on the achievability estimate on a display of or operatively connected with the computer.

11. The non-transitory storage medium of claim 10 wherein the computing includes computing a geometric complexity (GC) metric comprising a ratio comparing n and $N=N_T/V$ where V is the volume of the target volume.

12. The non-transitory storage medium of claim 11 wherein the achievability estimate comprises computing a GC ratio of (i) the GC metric for the IMRT geometry and (ii) the GC metric for a reference IMRT geometry.

13. The non-transitory storage medium of claim 10 wherein the radiation therapy planning method further comprises:
selecting at least one reference IMRT plan by comparing the achievability estimate for the IMRT geometry with reference achievability estimates computed for IMRT plans stored in a reference IMRT plans database;
wherein the displaying includes displaying information about the selected at least one reference IMRT plan.

14. The non-transitory storage medium of claim 10 wherein the achievability estimate is computed not based on any dose objective.

15. A radiation therapy planning method comprising:
using a computer, computing an achievability estimate for an intensity modulated radiation therapy (IMRT) geometry, wherein the IMRT geometry for which the achievability estimate is computed includes a target volume to be irradiated, an organ at risk (OAR), and at least one radiation beam, the computing including:
computing a geometric complexity (GC) metric for the IMRT geometry that compares a number $N_T$ of beamlets of the at least one radiation beam available in the IMRT geometry for irradiating the target volume and a number n of the $N_T$ beamlets that also pass through the OAR,
computing a GC metric ratio of (i) the GC metric for the IMRT geometry and (ii) the GC metric for a reference IMRT geometry for which an IMRT plan is known to be achievable; and
displaying the achievability estimate on a computer display.

16. The radiation therapy planning method of claim 15 wherein the GC metric is a ratio comparing n and $N=N_T/V$ where V is the volume of the target volume.

17. The radiation therapy planning method of claim 15 wherein the GC metric does not depend on any dose objective.

18. The radiation therapy planning method of claim 15 further comprising:
performing optimization of an IMRT plan for the IMRT geometry to determine at least one multileaf collimator (MLC) configuration for modulating the beamlets of the at least one radiation beam in the IMRT geometry to achieve a dose objective for the target volume and a maximum permissible dose objective for the OAR.

19. The radiation therapy planning method of claim 18 wherein the optimization is not started until after the displaying of the achievability estimate on the computer display.

20. The radiation therapy planning method of claim 15 further comprising:
- repeating the computing of an achievability estimate for a plurality of IMRT geometries each including the same target volume and the same at least one radiation beam and each including a different OAR; and
- adjusting one or more geometrical parameters of the at least one radiation beam to optimize an objective function comprising a weighted sum of the achievability estimates.

* * * * *